US012398367B2

United States Patent
Castaing et al.

(10) Patent No.: US 12,398,367 B2
(45) Date of Patent: *Aug. 26, 2025

(54) USE OF CATIONIC HYDROXYALKYL GUARS FOR MICROORGANISMS GROWTH

(71) Applicant: SPECIALTY OPERATIONS FRANCE, Lyons (FR)

(72) Inventors: Jean-Christophe Castaing, Sèvres (FR); Florence Lambert, Paris (FR); Clara Vernay, Paris (FR); Marina Gabriel Pessoa, São Paulo (BR)

(73) Assignee: SPECIALTY OPERATIONS FRANCE, Lyons (FR)

( * ) Notice: Subject to any disclaimer, the term of this patent is extended or adjusted under 35 U.S.C. 154(b) by 921 days.

This patent is subject to a terminal disclaimer.

(21) Appl. No.: 17/298,326

(22) PCT Filed: Nov. 29, 2019

(86) PCT No.: PCT/EP2019/083108
§ 371 (c)(1),
(2) Date: May 28, 2021

(87) PCT Pub. No.: WO2020/109560
PCT Pub. Date: Jun. 4, 2020

(65) Prior Publication Data
US 2022/0025320 A1 Jan. 27, 2022

(30) Foreign Application Priority Data
Nov. 29, 2018 (EP) .................................... 18209213

(51) Int. Cl.
| | | |
|---|---|---|
| *A01N 25/00* | (2006.01) | |
| *A01N 43/16* | (2006.01) | |
| *A01N 63/20* | (2020.01) | |
| *A01N 63/22* | (2020.01) | |
| *A01N 63/23* | (2020.01) | |
| *A01N 63/27* | (2020.01) | |
| *A01N 63/34* | (2020.01) | |
| *A01N 63/38* | (2020.01) | |
| *C12N 1/14* | (2006.01) | |
| *C12N 1/20* | (2006.01) | |
| *C12N 1/38* | (2006.01) | |

(52) U.S. Cl.
CPC ............... *C12N 1/38* (2013.01); *A01N 43/16* (2013.01); *A01N 63/20* (2020.01); *A01N 63/22* (2020.01); *A01N 63/23* (2020.01); *A01N 63/27* (2020.01); *A01N 63/34* (2020.01); *A01N 63/38* (2020.01); *C12N 1/14* (2013.01); *C12N 1/20* (2013.01)

(58) Field of Classification Search
CPC ... C12N 1/38; C12N 1/14; C12N 1/20; A01N 63/20; A01N 63/22; A01N 63/23; A01N 63/27; A01N 63/34; A01N 63/38
See application file for complete search history.

(56) References Cited

U.S. PATENT DOCUMENTS

| | | | |
|---|---|---|---|
| 4,031,307 A | 6/1977 | DeMartino | |
| 2022/0017857 A1* | 1/2022 | Castaing | ................ A01N 63/30 |
| 2022/0046928 A1* | 2/2022 | Castaing | ................ A01N 63/22 |

FOREIGN PATENT DOCUMENTS

| | | | | |
|---|---|---|---|---|
| CN | 107889970 A | 6/1977 | | |
| WO | WO-2006018305 A2 * | 2/2006 | ............. | B01F 5/045 |
| WO | 2012118795 A2 | 9/2012 | | |
| WO | 2014005319 A1 | 1/2014 | | |
| WO | WO-2016101862 A1 * | 6/2016 | ............... | A01C 5/06 |
| WO | WO-2017089641 A1 * | 6/2017 | | |

OTHER PUBLICATIONS

Banerjee, Chiranjib, et al. "Study of algal biomass harvesting using cationic guar gum from the natural plant source as flocculant." Carbohydrate polymers 92.1 (2013): 675-681. (Year: 2013).*
Mateen, Abdul, et al. "Suitability of various plant derived gelling agents as agar substitute in microbiological growth media." African Journal of Biotechnology 11.45 (2012): 10362-10367. (Year: 2012).*
Waikhom Gangotri et al: "Evaluation of guar gum derivatives as gelling agents for microbial culture media", World Journal of Microbiology and Biotechnology., vol. 28, No. 5, Mar. 2 201Z (Mar. 2, 2012), pp. Z279-2Z85, XP055661842, GB ISSN: 8959-3993, DOI: 10.1067/s11274-612-1627-8 pp. 2279-2285.
U.S. Appl. No. 17/298,272, filed May 28, 2021.
U.S. Appl. No. 17/298,283, filed May 28, 2021.
U.S. Appl. No. 17/298,290, filed May 28, 2021.
U.S. Appl. No. 17/298,310, filed May 28, 2021.

* cited by examiner

*Primary Examiner* — Abigail Vanhorn
(74) *Attorney, Agent, or Firm* — Osha Bergman Watanabe & Burton LLP

(57) ABSTRACT

The present invention relates to the in vitro use of a cationic hydroxyalkyl guar for maintaining or increasing the growth rate of microorganisms, wherein said cationic hydroxyalkyl guar has an average molecular weight of between 2,000 Daltons and 90,000 Daltons.

18 Claims, No Drawings

USE OF CATIONIC HYDROXYALKYL GUARS FOR MICROORGANISMS GROWTH

This application is a U.S. national phase entry under 35 U.S.C. § 371 of International Application No. PCT/EP2019/083108, filed on Nov. 29, 2019 which claims priority to European patent application No. 18209213.0 filed on Nov. 29, 2018. The entire contents of these applications are explicitly incorporated herein by this reference.

The present invention concerns the use of cationic hydroxyalkyl guars for the growth of microorganisms, in particular of bacteria.

The microorganisms may have beneficial effects for the medium with which they may interact. It is thus useful to sow such medium with these microorganisms. Once the microorganisms are deposited on the target medium, they need to grow and thus survive in a specific environment, wherein a bacterial flora already exists. It is thus essential for the microorganisms to still be able to grow and reproduce in the target medium despite the presence of this bacterial flora.

The skilled person thus seeks ingredients which may be used in formulations, such as in phytosanitary formulations, which would create an environment which would improve the growth of the microorganisms.

Due to the increase of the worldwide population growth, the food needs are thus increasing. Biostimulants are thus increasingly used in the world agricultural production.

The speed with which the plant roots reach nutrients is a critical parameter in the successful initial plant development and growth, usually in the first few weeks. Biostimulants help improve plant growth by providing nutrients from natural products or by helping plants to access nutrients.

Biostimulants promote plant growth and development throughout the life cycle of the crop, from seed germination to plant maturity. They improve the efficiency of plant metabolism leading to increased breeding and better quality. They increase plant tolerance to abiotic stress and the ability to recover. They facilitate the assimilation, passage and use of nutrients. They improve the quality of agricultural production, including the sugar content, the color and the size of the fruit. In addition, they regulate and improve the water content of plants. Finally, they increase certain physico-chemical properties of the soil and promote the development of micro-organisms on the ground.

The use of microorganisms or microorganism cocktails for plant biostimulation is well known. These methods are based on the application of compositions containing a purified microorganism or a mixture of microorganisms. Such compositions contain in particular *Bacillus* strains.

To date, the main drawback concerning the use of microorganisms as plant biostimulants is the difficulty to maintain such activity.

There is thus a need to find means to maintain or even improve the activity and efficiency of biostimulants such as microorganisms, in particular of bacteria.

There is also a need to find means to specifically maintain or improve the growth of a target microorganism in a given medium.

Therefore, the present invention relates to the in vitro use of a cationic hydroxyalkyl guar for maintaining or increasing the growth rate of microorganisms, wherein said cationic hydroxyalkyl guar has an average molecular weight of between about 2,000 Daltons and about 90,000 Daltons.

According to the invention, the growth rate of microorganisms, in particular of bacteria, may be measured by the following method:

Microorganisms are incubated in a culture media in presence of guar. Sampling is performed at different times in order to determine the number of colony forming unit (CFU) using the spread-plating method. With this methodology, the evolution of the number of bacterial cells (expressed as CFU) as a function of time is obtained. The microorganism growth follows an exponential law: $N_t = N_0 e^{(\mu t)}$ with $\mu$ the growth rate of microorganisms. The value of the growth rate of microorganisms $\mu$ is obtained by fitting the experimental data in logarithmic scale, it corresponds to the slope of the evolution of $\ln(N_t)$ as a function of time (linear plot: $\ln(N_t) = \ln(N_0) + \mu t$).

According to an embodiment, the present invention relates to the in vitro use of a cationic hydroxyalkyl guar for maintaining or increasing the growth rate of microorganisms, wherein said cationic hydroxyalkyl guar has an average molecular weight of between about 2,000 Daltons and about 90,000 Daltons.

The present invention is thus based on the use of a cationic hydroxyalkyl guar which enables to maintain and keep constant over the time the biostimulant effect of microorganisms, in particular of bacteria, and in other words to maintain the growth rate of microorganisms, and in particular to maintain the bacterial growth rate.

Advantageously, the use of said cationic hydroxyalkyl guar enables to increase the biostimulant effect of microorganisms, in particular of bacteria, in other words to increase the growth rate of microorganisms, and in particular to increase the bacterial growth rate.

Preferably, according to the invention, when using the cationic hydroxyalkyl guar as defined above, the growth rate of microorganisms is increased of at least 5%, preferably of at least 10%, in comparison to the growth rate of microorganisms when no cationic hydroxyalkyl guar is used.

According to an embodiment, the present invention relates to the in vitro use of a cationic hydroxyalkyl guar for increasing the growth rate of microorganisms, wherein said cationic hydroxyalkyl guar has an average molecular weight of between about 2,000 Daltons and about 90,000 Daltons.

The present invention also relates to the use of a cationic hydroxyalkyl guar for maintaining or increasing the growth rate of microorganisms on a plant, on a seed or in the soil, wherein said cationic hydroxyalkyl guar has an average molecular weight of between 2,000 Daltons and 90,000 Daltons.

The present invention also relates to the use of a cationic hydroxyalkyl guar for maintaining or increasing the growth rate of bacteria on a plant, on a seed or in the soil, wherein said cationic hydroxyalkyl guar is as defined above.

According to an embodiment, the present invention thus concerns the agrochemical and more particularly the phytosanitary field. According to an embodiment, the cationic hydroxyalkyl guar as mentioned above is used on a plant, on a seed or in the soil.

Throughout the description, including the claims, the term "comprising one" or "comprising a" should be understood as being synonymous with the term "comprising at least one", unless otherwise specified, "between" and "from . . . to . . . " should be understood as being inclusive of the limits.

As used herein, "weight percent," "wt %," "percent by weight," "% by weight," and variations thereof refer to the concentration of a substance as the weight of that substance divided by the total weight of the composition and multiplied by 100.

Should the disclosure of any patents, patent applications, and publications which are incorporated herein by reference conflict with the description of the present application to the extent that it may render a term unclear, the present description shall take precedence.

Guars

Guars are polysaccharides composed of the sugars galactose and mannose. The backbone is a linear chain of β 1,4-linked mannose residues to which galactose residues are 1,6-linked at every second mannose in average, forming short side units.

Within the context of the present invention, "cationic guar" means a cationic derivative of a guar. "Cationic" means permanently positively charged whatever the pH or non permanently charged, e.g. a derivative that can be cationic below a given pH and neutral above that pH. Notably, the cationic guar is a chemically modified guar derivative which shows or potentially shows a net positive charge in a pH neutral aqueous medium.

The cationic guars of the present invention can be obtained by chemically modifying guars, generally natural guars, by using cationic etherifying agents. Suitable cationic etherifying agents include primary, secondary or tertiary amino groups or quaternary ammonium, sulfonium or phosphonium groups. Notably, the cationic etherifying agents are quaternary ammonium salts.

Preferably, the cationic etherifying agents are quaternary ammonium salts bearing three radicals, which may be identical or different, chosen from hydrogen, an alkyl radical containing 1 to 22 carbon atoms, more particularly 1 to 14, and advantageously 1 to 3 carbon atoms. The counterion is generally a halogen, which in one embodiment is chlorine.

"Alkyl" as used herein means a straight chain or branched saturated aliphatic hydrocarbon group and is intended to include both "unsubstituted alkyl" and "substituted alkyl", the latter of which refers to alkyl moieties having substituents (such as hydroxyl group and halogen group) replacing a hydrogen on one or more carbon atoms of the alkyl group.

The quaternary ammonium salts may be, for example: 3-chloro-2-hydroxypropyl trimethyl ammonium chloride (CHPTMAC), 2,3-epoxypropyl trimethyl ammonium chloride (EPTAC), diallyldimethyl ammonium chloride (DMDAAC) or other cationic reagents such as trimethylammoniumpropyl methacrylamide.

A typical cationic functional group in these cationic guars is trimethylammonium (2-hydroxyl) propyl, with a counter ion. Various counter ions can be utilized, including but not being limited to halides, such as chloride, fluoride, bromide, and iodide, sulfate, methylsulfate, and mixtures thereof.

The cationic hydroxyalkyl guar of the present invention may be chosen in the group consisting of cationic hydroxyalkyl guars, such as cationic hydroxyethyl guar, cationic hydroxypropyl guar, cationic hydroxybutyl guar.

In some aspects, the cationic hydroxyalkyl guar of the present invention is guar hydroxypropyltrimonium chloride or hydroxypropyl guar hydroxypropyltrimonium chloride, notably, guar hydroxypropyltrimonium chloride.

The degree of hydroxyalkylation (molar substitution or MS) of cationic hydroxyalkyl guars, that is the number of alkylene oxide molecules consumed by the number of free hydroxyl functions present on the guar, may be comprised between 0.1 and 3, preferably between 0.1 and 1.7. As example, a MS of 1 may represent one ethylene oxide unit per monosaccharide unit. According to an embodiment, the degree of hydroxyalkylation (molar substitution or MS) of cationic hydroxyalkyl guars is comprised between 0.1 and 1.7, preferably between 0.2 and 1.0.

According to an embodiment, the Degree of Substitution (DS) of cationic hydroxyalkyl guars, that is the average number of hydroxyl groups substituted per sugar unit, is comprised between 0.005 and 3. DS may notably be determined by titration. The cationic hydroxyalkyl guar of the present invention may have a DS of between 0.005 and 2. Preferably, the cationic hydroxyalkyl guar of the present invention has a DS of between 0.005 and 1. More preferably, the cationic hydroxyalkyl guar of the present invention has a DS of between 0.12 and 0.5.

The Charge Density (CD) of cationic hydroxyalkyl guars may be comprised between 0.01 and 4.9 meq/g, preferably between 0.4 and 2.1 meq/g. The charge density refers to the ratio of the number of positive charges per gram of polymer. For example, CD=1 meq/g means there are 0.001 charges per gram of polymer. The charge density multiplied by the polymer molecular weight determines the number of positively charged sites on a given polymer chain.

According to the present invention, the cationic hydroxyalkyl guar may have an average molecular weight (Mw) of between about 2,000 Daltons and 90,000 Daltons, preferably, the cationic hydroxyalkyl guar has an average molecular weight of between about 5,000 Daltons and 90,000 Daltons, more preferably, the cationic hydroxyalkyl guar has an average molecular weight of between about 5,000 Daltons and 60,000 Daltons, still more preferably, the cationic hydroxyalkyl guar has an average molecular weight of between about 5,000 Daltons and 50,000 Daltons, preferably of between about 5,000 Daltons and 40,000 Daltons.

According to another embodiment, the cationic hydroxyalkyl guar of the invention may have an average molecular weight (Mw) of between 100,000 Daltons and 4,500,000 Daltons, for instance between 500,000 Daltons and 4,000,000 Daltons, for instance between 1,000,000 Daltons and 3,500,000 Daltons, for instance between 2,000,000 and 3,500,000 Daltons.

The average molecular weight of the cationic hydroxyalkyl guar may be measured by GPC (Gel Permeation Chromatography). Measurements may be carried out for instance using Shodex OH Pak columns and Agilent Refractive Index Detector.

The cationic hydroxyalkyl guar according to the present invention may be prepared by depolymerizing cationically modified guars that have high molecular weight, so as to "split" the guar polymers to desired sizes. It is appreciated that the cationic hydroxyalkyl guar of the present invention may also be prepared by depolymerisation of natural guars, followed by cationization reactions to provide the polymers with cationic functionality. Various depolymerisation methods are well known in the art and may be used for the present invention, such as treatment by using peroxo compound (e.g., hydrogen peroxide) and irradiation. Examples of such methods are disclosed in U.S. Pat. Nos. 4,547,571, 6,383,344 and 7,259,192.

The cationization of guars can be easily made by a skilled person using methods commonly known in the art. Various methods for providing guar gums with cationic functionality are known in the art, for example as disclosed in U.S. Pat. Pub. No. 2008/0112907. Various methods for cross-linking guars with and without cationic modification of the guars are also known, see for example U.S. Pat. Nos. 5,532,350 and 5,801,116. Alternatively, low molecular weight guars can be obtained by harvesting guar beans which are still at an early developmental stage such that the harvested guar beans contain low molecular weight natural guar gums. Then the guar gums may be subject to cationization to provide them with cationic functionality.

The cationic hydroxyalkyl guars as defined above may be used in a composition.

The composition containing the cationic hydroxyalkyl guar may be a solid or a liquid composition. In the case wherein the composition is solid, the composition may be in the form of a powder, a particle, an agglomerate, a flake, a granule, a pellet, a tablet, a brick, a paste, a block such as a molded block, a unit dose, or another solid form known to those of skill in the art. Preferably, the solid composition is in the form of a powder or a granule.

In some aspects, the composition containing the guar is in the form of a granule. Granules containing the cationic hydroxyalkyl guar may be prepared in a three-step procedure: wet granulation followed by drying and sieving. The wet granulation step notably involves introduction and mixing of cationic hydroxyalkyl guar powders and a carrier, and optionally other ingredients, in granulation equipment (such as a mixing granulator). The mixing is conducted with spraying of water to the mixture. The wet granulation step will yield wet granules containing the cationic hydroxyalkyl guars. The weight ratio between the carrier and the cationic hydroxyalkyl guar which are to be mixed may be between 20:1 to 1:1, preferably, between 20:1 to 10:1. The water content introduced may be comprised between 10 wt % to 50 wt % based on the total weight of the wet granules. The carrier may be silicon dioxide, amorphous silica, precipitated silica, hydrated amorphous silica, precipitated silica, hydrated amorphous synthetic calcium silicate, hydrofobized precipitated silica, silica gel, sodium aluminium silicate, clay, zeolite, bentonite, layered silicate, caolim, sodium carbonate, sodium bicarbonate, sodium sulfate, sodium tripolyphosphate, sodium chloride, sodium silicate (water glass), magnesium chloride, calcium chloride, ammonium chloride, magnesium sulfate, calcium carbonate, calcium oxide, and/or calcium sulphate, or a mixture thereof. Notably, the carrier is selected from calcium chloride and calcium carbonate. The drying step notably involves drying the wet granules by using hot air flow. This step can usually be conducted in a fluid bed equipped with an air inlet and an air outlet. The sieving step may be conducted by using a vibrating plate.

The granules may have a diameter of 0.1 to 6 mm. Generally, normal granules have a diameter of 2-6 mm and micro granules have a diameter of 0.1-2 mm. Preferably, micro granules having a diameter of 0.5-1.6 mm are used.

Alternatively, the granules containing the cationic hydroxyalkyl guar may be prepared by using extrusion methods well known by a person skilled in the art. The extrusion methods are described in U.S. Pat. No. 6,146,570. For example, the cationic hydroxyalkyl guar and the carrier, and optionally other ingredients, may be blended with heating. The weight ratio between the carrier and the cationic hydroxyalkyl guar may be between 20:1 to 1:1. Then a binder may be melted and introduced into the mixture of the cationic hydroxyalkyl guar and the carrier. Then, an extrusion step may be carried out with extruder temperature maintained between 55° C. and 65° C. The soft warm granules may be formed and may be subsequently cooled below solidification point of the molten binder (at room temperature for instance) in order to obtain solid granules.

In the case that the seed treatment composition is liquid, the liquid composition may be a suspension, a dispersion, a slurry, a solution in a liquid carrier selected from water, organic solvents oils or a mixture thereof. The liquid composition may be prepared by mixing the cationic hydroxyalkyl guars as described above with the liquid carrier, optionally with other components, by using conventional methods. Preferably, the liquid composition is in the form of an aqueous solution. The composition may comprise from 1 wt % to 60 wt % of the cationic hydroxyalkyl guar based on the total weight of the composition. Preferably, the composition comprises from 5 wt % to 35 wt % of the cationic hydroxyalkyl guar based on the total weight of the composition. In some aspects, the composition comprises from 20 wt % to 30 wt % of the cationic hydroxyalkyl guar based on the total weight of the composition. When conducting seed treatment in industrial scale, it is preferred that the liquid composition used for the seed treatment contains high concentration of the cationic hydroxyalkyl guar, so that less volume of the liquid composition is required to achieve the desired dosage for the treatment (i.e. the weight ratio of the cationic hydroxyalkyl guar to the seeds being treated). Using small volume of the liquid composition can save costs and is less tedious. However, when the concentration of the cationic hydroxyalkyl guar in the liquid composition increases, the fluidity of the liquid composition will significantly decrease. As a result, the liquid composition may become too "thick" to be effectively applied to the seed or the soil, and has poor ability to spread on the surface of the seed or in the soil as well. For example, an aqueous composition comprising 3 wt % of a high molecular weight cationic hydroxyalkyl guar may already be very thick and thus have poor fluidity. One advantage of the present invention is that the cationic hydroxyalkyl guar according to the present invention has relatively low molecular weight. In such case, the resulting liquid composition can maintain excellent fluidity even if the cationic hydroxyalkyl guar is present at high concentrations, and therefore, such liquid composition can be conveniently used for treating the seeds or the soil. In one embodiment, the method of the present invention comprises a step in which the seed is coated with the composition as described above. Then the coated seed may be applied onto or in the soil, notably, in order to set in contact the coated seed with the ground.

Suitable coating techniques may be utilized to coat the seed or agglomeration of the seeds with the composition according to the present invention. Equipment that may be utilized for coating can include but are not limited to drum coaters, rotary coaters, tumbling drums, fluidized beds and spouted beds. It is appreciated that any suitable equipment or technique known by a person skilled in the art may be employed. The seed may be coated via a batch or continuous coating process. The seed may be coated with the composition according to the present invention which is either in solid form or liquid form. Preferably, an aqueous dispersion or solution is used.

The seeds may be separated prior to the coating step. In one embodiment, mechanical means, such as a sieve, may be employed for separating the seeds. The separated seeds can then be introduced into a coating machine having a seed reservoir. In one embodiment, the seeds are combined with the composition described herein, optionally with a binder and/or adhesive, in a mixing bowl.

In some aspects, one or more layers of coating which comprises the composition according to the present invention may be added onto the seeds or the agglomeration thereof. Outer layers can be introduced sequentially by coating the seeds or the agglomeration thereof in a rotating drum.

Agglomerators or agglomerator devices may also be utilized. Coating may be performed within a rotary coater by placing the seeds within a rotating chamber, which pushes the seeds against the inside wall of the chamber. Centrifugal forces and mixing bars placed inside the coater allow the seeds to rotate and mix with a coating layer comprising the composition according to the present invention. Binder or other coating materials can be pumped into the proximate center of the coater onto an atomizer disk that rotates along with the coating chamber. Upon hitting the atomizer disk, liquid adhesive is then directed outward in small drops onto the seeds.

Seed coating techniques also include, for example, placing the seeds in a rotating pan or drum. The seeds are then mist with water or other liquid, and then gradually a fine inert powder, e.g., diatomaceous earth, is added to the coating pan. Each misted seed becomes the center of a mass of powder, layers, or coatings that gradually increases in size. The mass is then rounded and smoothed by the tumbling action in the pan, similar to pebbles on the beach. The coating layers are compacted by compression from the weight of material in the pan. Binders often are incorporated near the end of the coating process to harden the outer layer of the mass. Binders can also reduce the amount of dust produced by the finished product in handling, shipping and sowing. Screening techniques, such as frequent hand screening, are often times utilized to eliminate blanks or doubles, and to ensure uniform size. For example, tolerance for seed coating compositions described herein can be +/−1/64 inch (0.4 mm), which is the US seed trade standard for sizing, established long before coatings were introduced. For example, coated lettuce seed is sown most frequently with a belt planter through an 8/64 inch (3.2 mm) diameter round holes in the belt. This hole size requires that the lettuce seeds coated with the composition according to the present invention can be sized over a 7.5/64 inch (3.0 mm) screen and through an 8.5/64 inch (3.4 mm) screen.

In one embodiment of the present invention, the seed may be contacted with the composition by using an "in situ coating" process, notably by implanting in a hole or a furrow in the soil a seed of a plant, and then applying the composition according to the present invention to surround or partially surround, or to be adjacent to the seed, so that the seed come into contact with the composition, notably with the cationic hydroxyalkyl guar. According to the invention, the hole may notably be a hole, a cavity or a hollowed area. The seed may be one that has not be treated by any agent, or a seed that has been treated with an agrochemical (such as fungicide and insecticide) and that has not been treated with the composition of the present invention. Preferably, the composition is deposited on the carrier to provide a granule or a micro granule before being applied. The granule or the micro granule containing the cationic hydroxyalkyl guar may be prepared by using the methods described above.

In still another embodiment, the cationic hydroxyalkyl guar according to the present invention (or the composition containing said cationic hydroxyalkyl guar) is administered to a soil in which a plant is cultivated. Then the seeds of the plant can be applied to the soil so that the seeds will come into contact with the composition, notably with the cationic hydroxyalkyl guar. Notably, the composition in liquid form, such as in the form of aqueous solution/dispersion, or the composition in solid form, such as in powder or granule, may be used.

Preferably, the application of the seed and the application of the composition according to the present invention are performed mechanically. It is appreciated that either or both of the referenced applications can be performed manually as well.

According to a preferred embodiment, the cationic hydroxyalkyl guar as defined above is used in a liquid form.

In one embodiment of the present invention, the cationic hydroxyalkyl guar is used in an amount ranging from 50 to 500 g/quintal seed.

Microorganisms

By "microorganism" is meant herein a microscopic organism, which may exist in its single-cell form or as a colony of cells. In a particular embodiment, said microorganism is unicellular.

The present invention relates more particularly to soil microorganisms, also known as soil microbes.

According to an embodiment, the microorganisms are fungi, in particular unicellular fungi, or bacteria.

In a particular embodiment, the microorganisms are bacteria.

According to an embodiment, the bacteria according to the invention are chosen from Gram-positive bacteria.

As used herein, the term "gram-positive bacteria" refers to bacterial cells which stain violet (positive) in the Gram stain assay. The Gram stain binds peptidoglycan which is abundant in the cell wall of gram-positive bacteria. In contrast, the cell wall of "gram-negative bacteria" has a thin layer of peptidoglycan, thus gram-negative bacteria do not retain the stain and allow to uptake the counterstain in the Gram stain assay.

Gram-positive bacteria are well-known from the skilled person and include bacteria from the *Actinobaculum, Actinomyces, Arthrobacter, Bifidobacterium, Frankia, Gardnerella, Lysinibacillus, Microbacterium, Micrococcus, Micromonospora, Mycobacterium, Nocardia, Rhodococcus, Streptomyces, Bacillus, Clostridium, Listeria, Enterococcus, Lactobacillus, Leuconostoc, Mycoplasma, Ureaplasma, Lactococcus, Paenibacillus, Pediococcus, Acetobacterium, Eubacterium, Heliobacterium, Heliospirillum* and *Sporomusa* genera.

In a particular embodiment, the Gram-positive bacteria are selected from the group consisting in *Actinobaculum, Actinomyces, Arthrobacter, Bifidobacterium, Frankia, Lysinibacillus, Microbacterium, Micrococcus, Micromonospora, Nocardia, Rhodococcus, Streptomyces, Bacillus, Listeria, Lactobacillus, Leuconostoc, Lactococcus, Paenibacillus, Pediococcus, Acetobacterium, Eubacterium, Heliobacterium, Heliospirillum* and *Sporomusa* genera bacteria.

In a particular embodiment, the Gram-positive bacteria are bacteria from the *Bacillus* genera, in particular bacteria selected from the group consisting of *Bacillus itcheniformis, Bacillus megaterium* (such as *B. megaterium* strain CCT 0536), *Bacillus pumilus* (such as *B. pumilus* strain GB34 (YieldShield; Bayer), *B. pumilus* strain QST2808 (Sonata; Bayer) and *B. pumilus* strain BU F-33), *Bacillus licheniformis* (such as *B. licheniformis* strain SB3086 (EcoGuard; Novozymes) and *B. licheniformis* strain DSM17236), *Bacillus oleronius, Bacillus mojavensis, Bacillus subtilis* (such as *B. subtilis* strains GB03 (Kodiak; Bayer), MBI 600 (Subtilex; Becker Underwood) and QST 713 (Serenade; Bayer), *B. subtilis* strain GB122 plus, *B. subtilis* strain EB120, *B. subtilis* strain J-P13, *B. subtilis* FB17, *B. subtilis* strains QST30002 and QST3004 (NRRL B-50421 and NRRLB-50455), *B. subtilis* strains QST30002 and QST3004 (NRRL B-50421 and NRRLB-50455) sandpaper mutants, *B. subtilis* strain QST 713, *B. subtilis* strain DSM 17231, *B. subtilis* strain KAS-001, *B. subtilis* strain KAS-006, *B. subtilis* strain KAS-009, *B. subtilis* strain KAS-010, *B. subtilis* strain KAS-011 and *B. subtilis* strain CCT0089), *Bacillus globisporus, Bacillus firmus* (such as *B. firmus* strain 1-1582 (Votivo and Nortica; Bayer)), *Bacillus thuringiensis* (such as *B. thuringiensis galleriae* strain SDS-502, *B. thuringiensis kurstaki* VBTS 2546 and *B. thuringiensis* subsp. *kurstaki* strain VBTS 2477 quadruple enterotoxin-deficient mutants), *Bacillus cereus* (such as *B. cereus* BP01), *Bacillus simplex*

(such as *B. simplex* strains 03WN13, 03WN23 and 03WN25), *Bacillus mycoides* (such as *B. mycoides* isolate BmJ NRRL B-30890), *Bacillus aryabhattai*, *Bacillus Plexus*, *Bacillus nealsonii*, *Bacillus sphaericus*, *Bacillus vallismortis* (such as *B. vallismortis* strain KAS-003), *Bacillus* methylotrophicus (such as *B. methylotrophicus* strain KAS-002, *B. methylotrophicus* strain KAS-005, *B. methylotrophicus* strain KAS-008, *B. methylotrophicus* strain KAS-012, *B. methylotrophicus* strain KAS-013 and *B. methylotrophicus* strain KAS-014), *Bacillus lentimorbus*, *Bacillus safensis*, and *Bacillus atrophaeus* (such as *B. atrophaeus* strain KAS-004) species; bacteria from the *Lysinibacillus* genera, in particular bacteria from the *Lysinibacillus sphaericus* species; bacteria from the *Microbacterium* genera, in particular bacteria from the *Microbacterium aurantiacum* species; bacteria from the *Paenibacillus* genera, in particular bacteria selected from the group consisting in *Paenibacillus polymyxa* and *Paenibacillus pulvifaciens* species; or bacteria from the *Streptomyces* genera, in particular bacteria from the *Streptomyces* K61 species.

In a more particular embodiment, the Gram-positive bacteria are bacteria from the *Bacillus* genera, in particular bacteria selected from the group consisting of *Bacillus itcheniformis*, *Bacillus megaterium* (such as *B. megaterium* strain CCT 0536), *Bacillus pumilus* (such as *B. pumilus* strain GB34 (YieldShield; Bayer), *B. pumilus* strain QST2808 (Sonata; Bayer) and *B. pumilus* strain BU F-33), *Bacillus licheniformis* (such as *B. licheniformis* strain SB3086 (EcoGuard; Novozymes) and *B. licheniformis* strain DSM17236), *Bacillus oleronius*, *Bacillus mojavensis*, *Bacillus subtilis* (such as *B. subtilis* strains GB03 (Kodiak; Bayer), MBI 600 (Subtilex; Becker Underwood) and QST 713 (Serenade; Bayer), *B. subtilis* strain GB122 plus, *B. subtilis* strain EB120, *B. subtilis* strain J-P13, *B. subtilis* FB17, *B. subtilis* strains QST30002 and QST3004 (NRRL B-50421 and NRRLB-50455), *B. subtilis* strains QST30002 and QST3004 (NRRL B-50421 and NRRLB-50455) sandpaper mutants, *B. subtilis* strain QST 713, *B. subtilis* strain DSM 17231, *B. subtilis* strain KAS-001, *B. subtilis* strain KAS-006, *B. subtilis* strain KAS-009, *B. subtilis* strain KAS-010, *B. subtilis* strain KAS-011 and *B. subtilis* strain CCT0089), *Bacillus globisporus*, *Bacillus firmus* (such as *B. firmus* strain 1-1582 (Votivo and Nortica; Bayer)), *Bacillus thuringiensis* (such as *B. thuringiensis galleriae* strain SDS-502, *B. thuringiensis kurstaki* VBTS 2546 and *B. thuringiensis* subsp. *kurstaki* strain VBTS 2477 quadruple enterotoxin-deficient mutants), *Bacillus cereus* (such as *B. cereus* BP01), *Bacillus simplex* (such as *B. simplex* strains 03WN13, 03WN23 and 03WN25), *Bacillus mycoides* (such as *B. mycoides* isolate BmJ NRRL B-30890), *Bacillus aryabhattai*, *Bacillus Plexus*, *Bacillus nealsonii*, *Bacillus sphaericus*, *Bacillus vallismortis* (such as *B. vallismortis* strain KAS-003), *Bacillus* methylotrophicus (such as *B. methylotrophicus* strain KAS-002, *B. methylotrophicus* strain KAS-005, *B. methylotrophicus* strain KAS-008, *B. methylotrophicus* strain KAS-012, *B. methylotrophicus* strain KAS-013 and *B. methylotrophicus* strain KAS-014), *Bacillus lentimorbus*, *Bacillus safensis*, and *Bacillus atrophaeus* (such as *B. atrophaeus* strain KAS-004) species.

In a more particular embodiment, the Gram-positive bacteria are bacteria from the *B. subtilis*, the *B. thuringiensis* or the *B. megaterium* species. In still a particular embodiment, the Gram-positive bacteria are *B. subtilis* CCT 0089, *B. thuringiensis* CCT 2335 or *B. megaterium* CCT 0536.

According to an embodiment, the bacteria according to the invention are chosen from Gram-negative bacteria.

Gram-negative bacteria are well-known from the skilled person and include bacteria from the *Acetobacter*, *Achromobacter*, *Actinobacillus*, *Agrobacterium*, *Allorhizobium*, *Azospirillum*, *Azotobacter*, *Bordetella*, *Bradyrhizobium*, *Brucella*, *Burkholderia*, *Campylobacter*, *Carbophilus*, *Chelatobacter*, *Chryseobacterium*, *Citrobacter*, *Delftia*, *Enterobacter*, *Erwinia*, *Escherichia*, *Flavobacterium*, *Francisella*, *Frateuria*, *Gluconobacter*, *Helicobacter*, *Haemophilus*, *Kalstia*, *Klebsiella*, *Legionella*, *Mesorhizobium*, *Moraxella*, *Neisseria*, *Pantoea*, *Pasteurella*, *Phyllobacterium*, *Proteus*, *Pseudomonas*, *Rhizobium*, *Salmonella*, *Serratia*, *Shigella*, *Sinorhizobium*, *Treponema*, *Vibrio*, *Xanthomonas* and *Yersinia* genera.

In a particular embodiment, the Gram-negative bacteria are selected from the group consisting in *Acetobacter*, *Achromobacter*, *Agrobacterium*, *Allorhizobium*, *Azospirillum*, *Azotobacter*, *Bradyrhizobium*, *Carbophilus*, *Chelatobacter*, *Delftia*, *Erwinia*, *Flavobacterium*, *Frateuria*, *Gluconobacter*, *Mesorhizobium*, *Neisseria*, *Pantoea*, *Phyllobacterium*, *Pseudomonas*, *Rhizobium*, *Serratia*, *Sinorhizobium* and *Xanthomonas* genera bacteria.

In a particular embodiment, the Gram-negative bacteria are bacteria from the *Acetobacter* genera, in particular bacteria from the *Acetobacter xylinum* species; bacteria from the *Agrobacterium* genera, in particular bacteria selected from the group consisting in *Agrobacterium radiobacter* (such as *A. radiobacter* strain k84 and *A. radiobacter* strain CCT 4774), *Agrobacterium rhizogenes*, *Agrobacterium rubi* and *Agrobacterium tumefaciens* species; bacteria from the *Azospirillum* genera, in particular bacteria selected from the group consisting in *Azospirillum brasilense*, *Azospirillum doebereinerae*, *Azospirillum halopraeferens*, *Azospirillum canadense*, *Azospirillum oryzae* and *Azospirillum lipoferum* species; bacteria from the *Azotobacter* genera, in particular bacteria selected from the group consisting in *Azotobacter chroococcum*, *Azotobacter vinelandii* and *Azotobacter salinestris* species; bacteria from the *Bradyrhizobium* genera, in particular bacteria selected from the group consisting in *Bradyrhizobium arachidis*, *Bradyrhizobium betae*, *Bradyrhizobium canariense*, *Bradyrhizobium cytisi*, *Bradyrhizobium daqingense*, *Bradyrhizobium denitrificans*, *Bradyrhizobium diazoefficiens*, *Bradyrhizobium elkanii*, *Bradyrhizobium embrapense*, *Bradyrhizobium erythrophlei*, *Bradyrhizobium ferriligni*, *Bradyrhizobium ganzhouense*, *Bradyrhizobium guangdongense*, *Bradyrhizobium huanghuaihaiense*, *Bradyrhizobium icense*, *Bradyrhizobium ingae*, *Bradyrhizobium iriomotense*, *Bradyrhizobium japonicum* (such as *B. japonicum* strain USDA110, *B. japonicum* bv. *genistearum*, *B. japonicum* bv. *glycinearum* and *B. japonicum* strain CCT 4065), *Bradyrhizobium jicamae*, *Bradyrhizobium kavangense*, *Bradyrhizobium lablabi*, *Bradyrhizobium liaoningense*, *Bradyrhizobium lupine*, *Bradyrhizobium manausense*, *Bradyrhizobium neotropicale*, *Bradyrhizobium oligotrophicum*, *Bradyrhizobium ottawaense*, *Bradyrhizobium pachyrhizi*, *Bradyrhizobium paxllaeri*, *Bradyrhizobium retamae*, *Bradyrhizobium rifense*, *Bradyrhizobium stylosanthis*, *Bradyrhizobium subterraneum*, *Bradyrhizobium tropiciagri*, *Bradyrhizobium valentinum*, *Bradyrhizobium viridifuturi*, and *Bradyrhizobium yuanmingense* species; bacteria from the *Delftia* genera, in particular bacteria from the *Delftia acidovorans* species; bacteria from the *Frateuria* genera, in particular bacteria from the *Frateuria aurantiaca* species; bacteria from the *Gluconobacter* genera, in particular bacteria from the *Gluconobacter diazotrophicus* species; bacteria from the *Mesorhizobium* genera, in particular bacteria from the *Mesorhizobium cicero* species; bacteria from the *Pseudomonas* genera, in particular bacteria selected from the group consisting in *Pseudomonas putida, Pseudomonas fluorescens, Pseudomonas protegens, Pseudomonas chlororaphis, Pseudomonas aurantiaca, Pseudomonas mendocina* and *Pseudomonas rathonis* species; bacteria from the *Rhizobium* genera, in particular bacteria selected from the group consisting in *Rhizobium leguminosarum, Rhizobium mongolense, Rhizobium bangladeshense, Rhizobium binae, Rhizobium gallicum, Rhizobium hainanense, Rhizobium indigoferae, Rhizobium lentis, Rhizobium loessense, Rhizobium lusitanum, Rhizobium phaseoli* and *Rhizobium lupine* species; or bacteria from the *Sinorhizobium* genera, in particular bacteria from the *Sinorhizobium meliloti* species.

In a more particular embodiment, the Gram-negative bacteria are bacteria from the *Agrobacterium* genera, in particular bacteria selected from the group consisting in *Agrobacterium radiobacter* (such as *A. radiobacter* strain k84 and *A. radiobacter* strain CCT 4774), *Agrobacterium rhizogenes, Agrobacterium rubi* and *Agrobacterium tumefaciens* species, or bacteria from the *Bradyrhizobium* genera, in particular bacteria selected from the group consisting in *Bradyrhizobium arachidis, Bradyrhizobium betae, Bradyrhizobium canariense, Bradyrhizobium cytisi, Bradyrhizobium daqingense, Bradyrhizobium denitrificans, Bradyrhizobium diazoefficiens, Bradyrhizobium elkanii, Bradyrhizobium embrapense, Bradyrhizobium erythrophlei, Bradyrhizobium ferriligni, Bradyrhizobium ganzhouense, Bradyrhizobium guangdongense, Bradyrhizobium huanghuaihaiense, Bradyrhizobium icense, Bradyrhizobium ingae, Bradyrhizobium iriomotense, Bradyrhizobium japonicum* (such as *B. japonicum* strain USDA110, *B. japonicum* bv. *genistearum, B. japonicum* bv. *glycinearum* and *B. japonicum* strain CCT 4065), *Bradyrhizobium jicamae, Bradyrhizobium kavangense, Bradyrhizobium lablabi, Bradyrhizobium liaoningense, Bradyrhizobium lupine, Bradyrhizobium manausense, Bradyrhizobium neotropicale, Bradyrhizobium oligotrophicum, Bradyrhizobium ottawaense, Bradyrhizobium pachyrhizi, Bradyrhizobium paxllaeri, Bradyrhizobium retamae, Bradyrhizobium rifense, Bradyrhizobium stylosanthis, Bradyrhizobium subterraneum, Bradyrhizobium tropiciagri, Bradyrhizobium valentinum, Bradyrhizobium viridifuturi,* and *Bradyrhizobium yuanmingense* species.

In more particular embodiments, the Gram-negative bacteria are bacteria from the *A. radiobacter*, the *B. japonicum* or the *P. putida* species. In still a particular embodiment, the Gram-negative bacteria are *A. radiobacter* strain CCT 4774, *B. japonicum* strain CCT 4065 or *P. putida* CCT 5357.

According to anyone of the invention embodiments, the microorganism may be for instance bacteria chosen from the *B. subtilis,* the *B. megaterium,* the *B. thuringiensis,* the *A. radiobacter,* the *B. japonicum* or the *P. putida* species.

According to another embodiment, the microorganisms are fungi, in particular unicellular fungi.

Fungi are well-known from the skilled person and include *Ascomycetes, Glomeromycetes* and *Basidiomycetes*. In a particular embodiment, said fungi are selected from the Ascomycetes phylum, in particular from the group consisting in the *Trichoderma, Metarhizium, Beauveria, Lecanicillium, Purpureocillium, Gliocladium, Isaria, Fusarium, Arthrobotrys, Penicillium, Aspergillus, Ampelomyces, Coniothyrium, Aureobasidium* and *Candida* genera; from the *Glomeromycetes* phylum, in particular from the group consisting in the *Glomus* and *Rhizophagus* genera; and/or from the *Basidiomycetes* phylum, in particular from the group consisting in the *Phlebiopsis* and *Rhizoctonia* genera.

In a particular embodiment, said fungi are fungi from the *Trichoderma* genera, in particular fungi selected from the group consisting in the *Trichoderma viride, Trichoderma atroviride, Trichoderma vixens, Trichoderma harzianum, Trichoderma hamatum, Trichoderma asperellum, Trichoderma koningii, Trichoderma longibrachiatum, Trichoderma ovalisporum, Trichoderma paucisporum, Trichoderma songyi, Trichoderma theobromicola* and *Trichoderma gamsii* species; fungi from the *Metarhizium* genera, in particular fungi selected from the group consisting in the *Metarhizium anisopliae, Metarhizium majus, Metarhizium brunneum* and *Metarhizium flavoviride* species; fungi from the *Beauveria* genera, in particular fungi from the *Beauveria bassiana* species; fungi from the *Lecanicillium* genera, in particular fungi selected from the group consisting in the *Lecanicillium lecanii* and *Lecanicillium muscarium* species; fungi from the *Purpureocillium* genera, in particular fungi from the *Purpureocillium lilacinum* species; fungi from the *Gliocladium* genera, in particular fungi from the *Gliocladium catenulatum* species; fungi from the *Isaria* genera, in particular fungi from the *Isaria fumosorosea* species; fungi from the *Fusarium* genera; fungi from the *Arthrobotrys* genera, in particular fungi from the *Arthrobotrys dactyloides* species; fungi from the *Penicillium* genera, in particular fungi selected from the group consisting in the *Penicillium bilaiae* and the *Penicillium digitatum* species; fungi from the *Aspergillus* genera, in particular fungi selected from the group consisting in the *Aspergillus awamori* and the *Aspergillus niger* species; fungi from the *Ampelomyces* genera, in particular fungi from the *Ampelomyces quisqualis* species; fungi from the *Coniothyrium* genera, in particular fungi from the *Coniothyrium minitans* species; fungi from the *Aureobasidium* genera, in particular fungi from the *Aureobasidium pullulans* species; fungi from the *Candida* genera, in particular fungi from the *Candida oleophila* species; fungi from the *Glomus* genera, in particular fungi selected from the group consisting in the *Glomus iranicum* and the *Glomus mosseae* species; fungi from the *Rhizophagus* genera, in particular fungi from the *Rhizophagus irregularis* species; fungi from the *Phlebiopsis* genera, in particular fungi from the *Phlebiopsis gigantea* species; or fungi from the *Rhizoctonia* genera, in particular fungi from the *Rhizoctonia solani* species.

In more particular embodiments, the fungi are fungi from the *Aspergillus niger, Trichoderma harzianum* or *Beauveria bassiana* species. In still a particular embodiment, the fungi are *Aspergillus niger* ATCC 16404 *Trichoderma harzianum* CCT 4790 or *Beauveria bassiana* ATCC 7159/DSM 1344.

According to anyone of the invention embodiments, the microorganism may be for instance bacteria chosen from the *B. subtilis,* the *B. megaterium,* the *B. thuringiensis,* the *A. radiobacter,* the *B. japonicum* or the *P. putida* species or fungi from the *A. niger, T. harzianum* or *B. bassiana* species, such as those described previously. It may be for instance bacteria chosen from the *B. subtilis,* the *B. megaterium,* the *B. thuringiensis,* the *B. japonicum* or the *P. putida* species or fungi from the *A. niger, T. harzianum* or *B. bassiana* species, such as those described previously.

The amount of microorganism to be used may vary from one microorganism to another and may also depend on the seed to be treated. In one embodiment of the present invention, the microorganism is used in an amount ranging from $1.10^4$ to $1.10^{15}$ CFU/quintal seed.

The present invention also relates to a method for maintaining or increasing the growth rate of microorganisms, in particular of bacteria, comprising a step of contacting at least one seed with a cationic hydroxyalkyl guar as defined above.

According to a preferred embodiment, this method is carried out in liquid medium. Therefore, preferably, this method comprises a step of contacting at least one seed with a cationic hydroxyalkyl guar as defined above in a liquid form or with a liquid composition comprising a cationic hydroxyalkyl guar as defined above.

The present invention also relates to the use of a microorganism, in particular a bacterium, and of a cationic hydroxyalkyl guar as defined above, as plant biostimulant. Therefore, the present invention relates to the combined use of said microorganism, in particular bacterium, and cationic hydroxyalkyl guar. It has been shown that the combination of said microorganism, in particular bacterium, and cationic hydroxyalkyl guar gives a plant biostimulant activity.

The present invention also relates to a biostimulant composition comprising at least one microorganism, in particular a bacterium, and at least one cationic hydroxyalkyl guar as defined above.

According to anyone of the invention embodiments, the microorganism and the cationic hydroxyalkyl guar are combined in a ratio microorganism:cationic hydroxyalkyl guar ranging from $1.10^4$ to $1.10^{15}$, for example ranging from $1.10^4$ to $1.10^{12}$, for example ranging from $1.10^4$ to $1.10^{11}$ CFU/g, for example ranging from $1.10^4$ to $5.10^{10}$ CFU/g, for example ranging from $1.10^5$ to $1.10^{10}$ CFU/g. For instance, the microorganism and the cationic hydroxyalkyl guar may be combined in a ratio microorganism: cationic hydroxyalkyl guar ranging from $1.10^8$ to $1.10^{12}$.

Preferably, this biostimulant composition is in a liquid form.

The present invention also relates to a kit comprising at least one microorganism, in particular a bacterium, and at least one cationic hydroxyalkyl guar as defined above, said kit being preferably used as plant biostimulant.

The present invention thus also relates to the use of the above-mentioned kit as plant biostimulant.

The present invention also relates to a seed coated with the biostimulant composition as defined above.

In one embodiment, the seed is of the crop or plant species including but not limited to corn (*Zea mays*), *Brassica* sp. (e.g., *B. napus, B. rapa, B. juncea*), alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus animus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (Macadamia *integrifolia*), almond (*Prunus amygdalus*), sugar beets (*Beta vulgaris*), sugarcane (*Saccharum* spp.), oats, barley, vegetables, ornamentals, woody plants such as conifers and deciduous trees, squash, pumpkin, hemp, zucchini, apple, pear, quince, melon, plum, cherry, peach, nectarine, apricot, strawberry, grape, raspberry, blackberry, soybean, sorghum, sugarcane, rapeseed, clover, carrot, and *Arabidopsis thaliana*.

In one embodiment, the seed is of any vegetables species including but not limited to tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), cauliflower, broccoli, turnip, radish, spinach, asparagus, onion, garlic, pepper, celery, and members of the genus *Cucumis* such as cucumber (*C. sativus*), cantaloupe (*C. cantalupensis*), and musk melon (*C. melo*).

In one embodiment, the seed is of any ornamentals species including but not limited to hydrangea (*Macrophylla hydrangea*), hibiscus (*Hibiscus rosasanensis*), petunias (*Petunia hybrida*), roses (*Rosa* spp.), azalea (*Rhododendron* spp.), tulips (*Tulipa* spp.), daffodils (*Narcissus* spp.), carnation (*Dianthus caryophyllus*), poinsettia (*Euphorbia pulchenima*), and chrysanthemum.

In one embodiment, the seed is of any conifer species including but not limited to conifers pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

In one embodiment, the seed is of any leguminous plant species including but not limited beans and peas. Beans include guar, locust bean, fenugreek, soybean, garden beans, cowpea, mungbean, lima bean, fava bean, lentils, chickpea, pea, moth bean, broad bean, kidney bean, lentil, dry bean, etc. Legumes include, but are not limited to, *Arachis*, e.g., peanuts, *Vicia*, e.g., crown vetch, hairy vetch, adzuki bean, mung bean, and chickpea, *Lupinus*, e.g., lupine, *trifolium*, *Phaseolus*, e.g., common bean and lima bean, *Pisum*, e.g., field bean, *Melilotus*, e.g., clover, *Medicago*, e.g., alfalfa, Lotus, e.g., trefoil, lens, e.g., lentil, and false indigo. Typical forage and turf grass for use in the methods described herein include but are not limited to alfalfa, orchard grass, tall fescue, perennial ryegrass, creeping bent grass, lucerne, birdsfoot trefoil, clover, stylosanthes species, lotononis bainessii, sainfoin and redtop. Other grass species include barley, wheat, oat, rye, orchard grass, guinea grass, sorghum or turf grass plant.

In another embodiment, the seed is selected from the following crops or vegetables: corn, wheat, sorghum, soybean, tomato, cauliflower, radish, cabbage, canola, lettuce, rye grass, grass, rice, cotton, sunflower and the like. In another embodiment, the seed is selected from corn, wheat, barley, rice, peas, oats, soybean, sunflower, alfalfa, sorghum, rapeseed, sugar beet, cotton, tobacco, forage crops, linseed, hemp, grass, vegetables, fruits and flowers seeds.

It is understood that the term "seed" or "seedling" is not limited to a specific or particular type of species or seed. The term "seed" or "seedling" can refer to seed from a single plant species, a mixture of seed from multiple plant species, or a seed blend from various strains within a plant species. In one embodiment, crop seeds include but are not limited to rice, corn, wheat, barley, oats, soybean, cotton, sunflower, alfalfa, sorghum, rapeseed, sugarbeet, tomato, bean, carrot, tobacco or flower seeds.

The following examples are included to illustrate embodiments of the invention, but is not limited to described examples.

EXAMPLES

Example 1

The following materials are used in the experiments:

Guar: a guar hydroxypropyltrimonium chloride having an average molecular weight between 5,000 and 25,000 Daltons, a DS of 0.2, and a MS between 0.2 and 1.0, available from Solvay (provided as a powder)

Bacteria strains were acquired from Tropical Culture Collection in André Tosello Foundation—Brazil.
*Bacillus subtilis* CCT 0089
*Bacillus megaterium* CCT 0536
*Bradyrhizobium japonicum* CCT 4065

All strains were stored at −80° C. in the appropriated culture media, containing 15% of glycerol.

Two different culture media were used in the experiments:
NA media containing per liter: 3 g of meat extract, 5 g of peptone and 15 g of agar (for solid media only)
YMA media containing per liter: 0.5 g of monobasic potassium phosphate, 0.2 g of magnesium sulphate; 0.1 g of sodium chloride; 0.5 g of yeast extract; 10 g of mannitol (for inoculum and solid media only); 5 mL of a 5% bromothymol blue solution and 15 g of agar (solid media only).

For strains *Bacillus subtilis* and *Bacillus megaterium*, NA media was used. For strain *Bradyrhizobium japonicum*, YMA media was used. These media were selected according to strains supplier.

A 250 mL shake flask containing 100 mL of NA or YMA culture media, was inoculated with 1 mL of the stock culture and incubated at 30° C., 150 rpm for 72 hours.

For each strain, 10 mL of the reactivation media were then transferred into a 250 mL shake flask containing 100 mL of the same media, with the addition of guar powder (at 1 wt % in the incubation media); and incubated at 30° C., 150 rpm, for 96 hours. An experiment without addition of guar powder is also performed for each strain as a control.

100 μL samples of each experiments were taken after 0 h, 24 h, 48 h, 72 h and 96 h of incubation. These samples were diluted (the dilutions were variable according to strain growth, being from $1 \times 10^{-5}$ up to $1 \times 10^{-15}$) and the dilutions plated in solid NA or YMA media. The plates were incubated at 30° C. until appearance of colonies. After incubation, the number of colonies present in each dilution was counted and used to evaluate bacterial growth.

For bacterial growth rate determination, a graph of the $\log_{10}$ (number of colonies) versus time of incubation was constructed. The straight line in this graph represents the exponential phase of bacterial growth and the angular coefficient represents the bacterial growth rate (O.

The μ value was used to compare all the experiments and to evaluate the influence of guar addition on bacterial growth.

For this set of experiments the ratio of microorganisms and guar is equal to $3.50 \times 10^4$ CFU/g. The bacteria growth rate (μ) obtained for the different experiments are summarized in Table 1:

TABLE 1

| Composition | Bacteria growth rate ($h^{-1}$) |
| --- | --- |
| *Bacillus subtilis* CCT 0089 | 0.0647 |
| *Bacillus subtilis* CCT 0089 + guar | 0.0739 |
| *Bacillus megaterium* CCT 0536 | 0.0605 |
| *Bacillus megaterium* CCT 0536 + guar | 0.0690 |
| *Bradyrhizobium japonicum* CCT 4065 | 0.0891 |
| *Bradyrhizobium japonicum* CCT 4065 + guar | 0.0880 |

For the three strains, a comparable or higher value of bacteria growth rate is obtained in presence of guar. The addition of guar permits to maintain or increase the growth rate of these different strains of bacteria. In Table 2 are reported the relative increase or decrease of bacteria growth rate with the addition of guar compared to the control for each strain. An increase of bacteria growth rate of +14% is observed for the two gram positive bacteria (*Bacillus subtilis* and *Bacillus megaterium*), whereas a nil value is observed for *Bradyrhizobium japonicum*, which correspond to a comparable growth rate of bacteria with and without guar.

TABLE 2

| Strain | Relative increase of bacteria growth rate with guar addition |
| --- | --- |
| *Bacillus subtilis* CCT 0089 | 14% |
| *Bacillus megaterium* CCT 0536 | 14% |
| *Bradyrhizobium japonicum* CCT 4065 | 0% |

A similar experiment was conducted at a ratio bacteria/guar equals to $7.00 \times 10^5$ on the same bacteria species, a comparable or higher value of bacteria growth is obtained in presence of guar.

Example 2

The following materials are used in the experiments:

Guar: a guar hydroxypropyltrimonium chloride having an average molecular weight between 5,000 and 25,000 Daltons, a DS of 0.2, and a MS between 0.2 and 1.0, available from Solvay (provided as a powder)

Liquid guar formulation: an aqueous formulation of the powder guar at 25% from Solvay Bacteria strains were acquired from Tropical Culture Collection in André Tosello Foundation—Brazil.
*Bacillus subtilis* CCT 0089
*Bacillus megaterium* CCT 0536
*Bradyrhizobium japonicum* CCT 4065

All strains were stored at −80° C. in the appropriated culture media, containing 15% of glycerol.

Two different culture media were used in the experiments:
NA media containing per liter: 3 g of meat extract, 5 g of peptone and 15 g of agar (for solid media only)
YMA media containing per liter: 0.5 g of monobasic potassium phosphate, 0.2 g of magnesium sulphate; 0.1 g of sodium chloride; 0.5 g of yeast extract; 10 g of mannitol (for inoculum and solid media only); 5 mL of a 5% bromothymol blue solution and 15 g of agar (solid media only).

For strains *Bacillus subtilis* and *Bacillus megaterium*, NA media was used. For strain *Bradyrhizobium japonicum*, YMA media was used. These media were selected according to strains supplier.

A 250 mL shake flask containing 100 mL of NA or YMA culture media, was inoculated with 1 mL of the stock culture and incubated at 30° C., 150 rpm for 72 hours.

For each strain, 10 mL of the reactivation media were then transferred into a 250 mL shake flask containing 100 mL of the same media, with the addition of guar powder or guar liquid formulation; and incubated at 30° C., 150 rpm, for 96 hours. An experiment without addition of guar powder is also performed for each strain as a control.

100 µL samples of each experiments were taken after 0 h, 24 h, 48 h, 72 h and 96 h of incubation. These samples were diluted (the dilutions were variable according to strain growth, being from $1 \times 10^{-5}$ up to $1 \times 10^{-15}$) and the dilutions plated in solid NA or YMA media. The plates were incubated at 30° C. until appearance of colonies. After incubation, the number of colonies present in each dilution was counted and used to evaluate bacterial growth.

For bacterial growth rate determination, a graph of the $\log_{10}$ (number of colonies) versus time of incubation was constructed. The straight line in this graph represents the exponential phase of bacterial growth and the angular coefficient represents the bacterial growth rate ($\mu$).

The $\mu$ value was used to compare all the experiments and to evaluate the influence of the two guars addition on bacterial growth. For this set of experiments the ratio of microorganisms and guar was set at $1.0 \times 10^{10}$ CFU/g. The bacteria growth rate ($\mu$) obtained for the different experiments are summarized in Table 3:

TABLE 3

| Composition | Bacteria growth rate ($h^{-1}$) |
|---|---|
| *Bacillus subtilis* CCT 0089 | 0.0862 |
| *Bacillus subtilis* CCT 0089 + guar powder | 0.0931 |
| *Bacillus subtilis* CCT 0089 + guar liquid formulation | 0.0975 |
| *Bacillus megaterium* CCT 0536 | 0.0834 |
| *Bacillus megaterium* CCT 0536 + guar powder | 0.1018 |
| *Bacillus megaterium* CCT 0536 + guar liquid formulation | 0.0958 |
| *Bradyrhyzobium japonicum* CCT 4065 | 0.0915 |
| *Bradyrhyzobium japonicum* CCT 4065 + guar powder | 0.0936 |
| *Bradyrhyzobium japonicum* CCT 4065 + guar liquid formulation | 0.0913 |

For the three strains, a comparable or higher value of bacteria growth rate is obtained in presence of the guar under powder form and the guar in aqueous formulation. The addition of guar permits to maintain or increase the growth rate of these different strains of bacteria. In Table 4 are reported the relative increase or decrease of bacteria growth rate with the addition of the two guar grades compared to the control for each strain. An increase of bacteria growth rate ranging from 8% to 22% is observed for the two gram positive bacteria (*Bacillus subtilis* and *Bacillus megaterium*), whereas a nil value or 2% is observed for *Bradyrhyzobium japonicum*, which correspond to a comparable growth rate of bacteria with and without guar.

TABLE 4

| Strain | Relative increase of bacteria growth rate with guar addition |
|---|---|
| *Bacillus subtilis* CCT 0089 + guar powder | 8% |
| *Bacillus subtilis* CCT 0089 + guar liquid formulation | 13% |
| *Bacillus megaterium* CCT 0536 + guar powder | 22% |
| *Bacillus megaterium* CCT 0536 + guar | 15% |

TABLE 4-continued

| Strain | Relative increase of bacteria growth rate with guar addition |
|---|---|
| liquid formulation | |
| *Bradyrhyzobium japonicum* CCT 4065 + guar powder | 2% |
| *Bradyrhyzobium japonicum* CCT 4065 + guar liquid formulation | 0% |

Example 3

The following materials are used in the experiments:

Guar: a guar hydroxypropyltrimonium chloride having an average molecular weight between 5,000 and 25,000 Daltons, a DS of 0.2, and a MS between 0.2 and 1.0, available from Solvay (provided as a powder)

Bacteria strains were acquired from Tropical Culture Collection in André Tosello Foundation—Brazil:
*Bacillus thuringiensis* CCT 2335
*Pseudomonas putida* CCT 2357

All strains were stored at −80° C. in the appropriate culture media, containing 15% of glycerol.

Only one culture media was used for both strains

NA media containing per liter: 3 g of meat extract, 5 g of peptone and 15 g of agar (for solid media only)

A 250 mL shake flask containing 100 mL of NA or YMA culture media, was inoculated with 1 mL of the stock culture and incubated at 30° C., 150 rpm for 72 hours.

For each strain, 10 mL of the reactivation media were then transferred into a 250 mL shake flask containing 100 mL of the same media, with the addition of guar powder or guar liquid formulation; and incubated at 30° C., 150 rpm, for 96 hours. An experiment without addition of guar powder is also performed for each strain as a control.

100 µL samples of each experiments were taken after 0 h, 24 h, 48 h, 72 h and 96 h of incubation. These samples were diluted (the dilutions were variable according to strain growth, being from $1 \times 10^{-5}$ up to $1 \times 10^{-15}$) and the dilutions plated in solid NA media. The plates were incubated at 30° C. until appearance of colonies. After incubation, the number of colonies present in each dilution was counted and used to evaluate bacterial growth.

For bacterial growth rate determination, a graph of the $\log_{10}$ (number of colonies) versus time of incubation was constructed. The straight line in this graph represents the exponential phase of bacterial growth and the angular coefficient represents the bacterial growth rate ($\mu$).

The $\mu$ value was used to compare all the experiments and to evaluate the influence of the two guars addition on bacterial growth. For this set of experiments the ratio of microorganisms and guar was set at $1.0 \times 10^{5}$ CFU/g. The bacteria growth rate ($\mu$) obtained for the different experiments are summarized in Table 5:

TABLE 5

| Composition | Bacteria growth rate ($h^{-1}$) |
|---|---|
| *Bacillus thuringiensis* CCT 2335 | 0.0898 |
| *Bacillus thuringiensis* CCT 2335 + guar | 0.1028 |
| *Pseudomonas putida* CCT 5357 | 0.1133 |
| *Pseudomonas putida* CCT 5357 + guar | 0.1282 |

For the two strains, a higher value of bacteria growth rate is obtained in the presence of guar than without guar addition. The addition of guar permits to increase the growth rate of these different strains of bacteria. In Table 6 are reported the relative increase of bacteria growth rate with the addition of guar compared to the control for each strain. An increase of bacteria growth rate ranging from 13% to 14% is observed for the two strains of bacteria.

TABLE 6

| Strain | Relative increase of bacteria growth rate with guar addition |
|---|---|
| *Bacillus thuringiensis* CCT 2335 | 14% |
| *Pseudomonas putida* CCT 5357 | 13% |

Example 4

The following materials are used in the experiments:

Guar: a guar hydroxypropyltrimonium chloride having an average molecular weight between 5,000 and 25,000 Daltons, a DS of 0.2, and a MS between 0.2 and 1.0, available from Solvay (provided as a powder)

Liquid guar formulation: an aqueous formulation of the powder guar at 25% from Solvay All microorganisms strains were acquired from Tropical Culture Collection in André Tosello Foundation—Brazil, some of them have reference in American Type Culture Colection (ATCC).

*Trichoderma harzianum* CCT 4790

*Aspergillus niger* ATCC 16404

All strains were stored at −80° C. in the appropriate culture media, containing 20% of glycerol.

Culture media used in the experiments:

Nutrient broth (NA) media containing per liter: 3 g of meat extract, 5 g of peptone and 15 g of agar (for solid media only)

Oatmeal Agar (OA) containing per liter: 25 g of oat flakes or flour and 15 g of agar Sabouraud dextrose agar (SDA) containing per liter: 40 g of glucose, 10 g of peptone and 20 g agar The media SDA and OA were used for reactivation of the strains *A. niger* and *T. harzianum* respectively, according to supplier's recommendation.

For the experiments with guar, only NA media was used.

Reactivation of Microorganisms:

A Petri dish containing 20 mL of SDA or OA media was used for the reactivation of the strains *A. niger* and *T. harzianum*, respectively.

The stock culture was used to inoculate the solid media for each strain and the petri dishes were incubated at 25° C. until complete growth.

Incubation with Guar:

From the reactivation media on petri dish, the spores of fungi were recovered and a spore solution was prepared.

500 µL of the spore solution (approximately $1\times10^{10}$ CFU/mL) were transferred to Erlenmeyer flasks containing 50 mL of media (controls and NA media with guar) and incubated at 25° C. Samples were taken at 48 h, 120 h and 168 h, filtered on filter paper and incubated at 60° C. before weighing Control media=NA without guar addition Growth Evaluation:

The dry biomass recovery after each sample was plotted in a graphic dry biomass vs time and the growth curve could be obtained.

The growth rate (g) was calculated considering only the exponential phase of the growth and compared with the control.

The µ value was used to compare all the experiments and to evaluate the influence of guar addition on fungi growth. The microorganisms growth rate (µ) obtained for the different experiments are summarized in Table 7:

TABLE 7

| Composition | Fungi growth rate ($h^{-1}$) |
|---|---|
| *Trichoderma harzianum* CCT 4790 | 0.0009 |
| *Trichoderma harzianum* CCT 4790 + guar powder | 0.0013 |
| *Trichoderma harzianum* CCT 4790 + guar liquid formulation | 0.0015 |
| *Aspergillus niger* ATCC 16404 | 0.0008 |
| *Aspergillus niger* ATCC 16404 + guar powder | 0.0014 |
| *Aspergillus niger* ATCC 16404 + guar liquid formulation | 0.0015 |

For the two strains, a higher value of growth rate is obtained in presence of the guar under powder form and the guar in aqueous formulation compared to control. Hence, the addition of guar permits to increase the growth rate of these different strains of fungi. In Table 8 are reported the relative increase of growth rate with the addition of the two guar grades compared to the control for each strain. An increase of bacteria growth rate ranging from 44% to 88% is observed for the two strains of fungi.

TABLE 8

| Strain | Relative increase of fungi growth rate with guar addition |
|---|---|
| *Trichoderma harzianum* CCT 4790 + guar powder | 44% |
| *Trichoderma harzianum* CCT 4790 + guar liquid formulation | 67% |
| *Aspergillus niger* ATCC 16404 + guar powder | 75% |
| *Aspergillus niger* ATCC 16404 + guar liquid formulation | 88% |

The invention claimed is:

1. A method, comprising contacting microorganisms with a cationic hydroxyalkyl guar in the presence of a culture medium in vitro or applying a biostimulant composition comprising microorganisms and the cationic hydroxyalkyl guar, to a plant, a seed or soil to increase growth of the microorganisms, wherein said cationic hydroxyalkyl guar has an average molecular weight of between 2,000 Daltons and 90,000 Daltons and said cationic hydroxyalkyl guar is present at a concentration to increase the growth rate of the microorganisms at least 5% compared to without the presence of the cationic hydroxyalkyl guar.

2. The method of claim 1, wherein the microorganisms are fungi or bacteria.

3. The method of claim 1, wherein the cationic hydroxyalkyl guar is obtained by chemically modifying a guar with a cationic etherifying agent.

4. The method of claim 3, wherein the cationic etherifying agent is a quaternary ammonium salt selected from the group consisting of: 3-chloro-2-hydroxypropyl trimethyl ammonium chloride, 2,3-epoxypropyl trimethyl ammonium chloride, diallyldimethyl ammonium chloride, and trimethylammoniumpropyl methacrylamide.

5. The method of claim 1, wherein the cationic hydroxyalkyl guar is selected from the group consisting of: cationic hydroxyethyl guar, cationic hydroxypropyl guar, cationic hydroxybutyl guar.

6. The method of claim 5, wherein the cationic hydroxyalkyl guar is guar hydroxypropyltrimonium chloride.

7. The method of claim 1, wherein the cationic hydroxyalkyl guar has a Degree of Substitution of between 0.005 and 1.

8. The method of claim 7, wherein the cationic hydroxyalkyl guar has a Degree of Substitution of between 0.12 and 0.5.

9. The method of claim 1, wherein the cationic hydroxyalkyl guar has an average molecular weight of between 5,000 Daltons and 90,000 Daltons.

10. The method of claim 9, wherein the cationic hydroxyalkyl guar has an average molecular weight between 5,000 Daltons and 60,000 Daltons.

11. The method of claim 1, wherein the cationic hydroxyalkyl guar has a degree of hydroxyalkylation comprised between 0.1 and 1.7.

12. The method of claim 11, wherein the cationic hydroxyalkyl guar has a degree of hydroxyalkylation comprised between 0.2 and 1.0.

13. The method of claim 1, comprising a step of contacting at least one seed with a cationic hydroxyalkyl guar having an average molecular weight of between 2,000 Daltons and 90,000 Daltons.

14. The method of claim 1, wherein the microorganisms are bacteria.

15. A biostimulant composition comprising at least one microorganism and at least one cationic hydroxyalkyl guar having an average molecular weight of between 2,000 Daltons and 90,000 Daltons, wherein said cationic hydroxyalkyl guar is present at a concentration to increase the growth rate of the microorganisms at least 5% compared to without the presence of the cationic hydroxyalkyl guar.

16. The biostimulant composition of claim 15, wherein the at least one microorganism is a bacterium.

17. A seed coated with the biostimulant composition of claim 15.

18. A kit comprising at least one microorganism and at least one cationic hydroxyalkyl guar having an average molecular weight of between 2,000 Daltons and 90,000 Daltons, wherein said cationic hydroxyalkyl guar is present at a concentration to increase the growth rate of the microorganisms at least 5% compared to without the presence of the cationic hydroxyalkyl guar.

* * * * *